United States Patent [19]

Fizet

[11] Patent Number: 4,596,879

[45] Date of Patent: Jun. 24, 1986

[54] PROCESS FOR PRODUCING INTERMEDIATE FURANONES FROM DIOL DERIVATIVE AND THIONYL CHLORIDE

[75] Inventor: Christian Fizet, Zimmersheim, France

[73] Assignee: Hoffmann-La Roche Inc., Nutley, N.J.

[21] Appl. No.: 753,493

[22] Filed: Jul. 10, 1985

[30] Foreign Application Priority Data

Jul. 27, 1984 [CH] Switzerland .................. 3660/84

[51] Int. Cl.$^4$ ................. C07D 327/10; C07D 307/32
[52] U.S. Cl. .................................. 549/295; 549/18; 549/319
[58] Field of Search ............. 549/18, 319, 295

[56] References Cited

FOREIGN PATENT DOCUMENTS 0718243 12/1968 Belgium ........................... 544/97
1213166 11/1970 United Kingdom ............ 544/97

OTHER PUBLICATIONS

Yamamoto, C.A., vol. 82, 1975, 82: 3820w, p. 329.
Brode et al., Index Chemicus, vol. 22, (5), Issue 154, Aug. 15, 1966, 68,430.
Lee et al., C.A., vol. 98, 1983, 98: 53128c, p. 604.
Houben-Weyl, Methodea Pen Organischen Chemile (1963), B and V½ pp. 656–657.
Windaus et al., Ber. 54, 581 (1921).
Pattison et al., J. Chem. Soc., 2745, (1949).
Oldham, J. Chem. Soc., 100 (1950).
Falbe et al., Ber. 97, 863 (1964).
Doyle et al., Tet. Letters 2795, (1980).
Doyle et al., Synthetic Comm., 10, 881 (1980).
Tomioka et al., Tet. Letters, 1605 (1981).

*Primary Examiner*—Henry R. Jiles
*Assistant Examiner*—J. G. Mullins
*Attorney, Agent, or Firm*—Jon S. Saxe; George M. Gould; William H. Epstein

[57] ABSTRACT

A novel process for the manufacture of the furanone of the formula

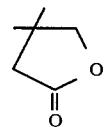

I is described. In this process, a diol is firstly reacted with thionyl chloride, then the sulphite formed, optionally after oxidation to the corresponding sulphate, is treated with sodium cyanide and the resulting hydroxynitrile is hydrolyzed.

The furanone of formula I can be used as a starting material for the manufacture of R-(−)-pantolactone.

7 Claims, No Drawings

PROCESS FOR PRODUCING INTERMEDIATE FURANONES FROM DIOL DERIVATIVE AND THIONYL CHLORIDE

The present invention is concerned with a novel process for the manufacture of the furanone of the formula

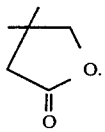   I

This furanone of formula I is a known compound which can be used, inter alia, as a starting material for the manufacture of optically active R-(−)-pantolactone.

The process in accordance with the invention comprises reacting the diol of the formula

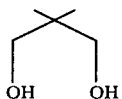   II with thionyl chloride to give the compound of the formula

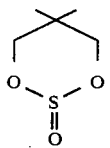   III if desired, oxidizing this compound to give the compound of the formula

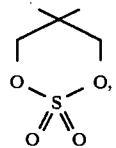   IV reacting the compound of formula III or IV with sodium cyanide and hydrolyzing the thus-obtained compound of the formula

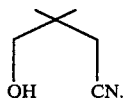   V

The diol of formula II used as the starting material and also the compounds of formulae III and IV are known compounds. The compound of formula V is, however, novel and is also an object of the present invention.

The reaction of the diol of formula II with thionyl chloride to give the compound of formula III can be carried out in a manner known per se. Conveniently, this reaction is carried out in an inert organic solvent and at a temperature of about −20° C. to about the reflux temperature of the reaction mixture, perferably at about 0° C. to about 60° C. As solvents there can be named, in particular: halogenated hydrocarbons such as methylene chloride, chloroform or carbon tetrachloride or also ethers such as diethyl ether, dioxan, tetrahydrofuran and the like. If desired, this reaction can also be carried out in the absence of a solvent.

The reaction of a compound of formula III with sodium cyanide is carried out in dimethyl sulphoxide and at a temperature of about 80° C. to about 120° C., preferably at about 100° C. The reaction is also conveniently carried out under an inert gas such as e.g. argon, nitrogen and the like.

The hydrolzysis of the compound of formula V can be carried out in a manner known per se, i.e. in a manner which is usual for the hydrolzysis of nitrile groups. Conveniently, this hydrolzysis is carried out by treating the compound of formula V with a mineral acid, for example hydrochloric acid, sulphuric acid or phosphoric acid and the like, at temperatures up to about the reflux temperature of the reaction mixture. The carboxylic acid which is formed in the hydrolzysis lactonizes spontaneously under the reaction conditions to the furanone of formula I.

The reaction of the compound of formula III with sodium cyanide and the subsequent hydrolzysis of the thusobtained compound of formula V can be carried out not only as described previously, but also without isolating the compound of formula V.

The oxidation of the compound of formula III to the compound of formula IV can be carried out in a manner known per se, i.e. in a manner analogous to the oxidation of organic sulphites. This is normally carried out using calcium permangante in an aqueous medium. Surprisingly, it has now also been found that this oxidation in the present case can also be carried out using potassium permangante in the presence of phase-transfer catalysts. Any conventional phase transfer catalyst can be used in carrying out this reaction. The preferred phase transfer catalyst are, for example, benzyltriethylammonium chloride or also tetrabutylammonium hydrogen sulphate and the like. As the organic solvent, any of the conventional inert organic solvents can be utilized, with those solvents utilized in the preparation of compound III being preferred. Furthermore, the oxidation is also conveniently carried out at a temperature of about 0° C. to about 20° C., preferably at about 5°–10° C.

The conversion of the compound of formula IV into the compound of formula V and into the furanone of formula I can be carried out in an analogous manner to the conversion of the compound of formula III. In the present case the direct conversion, i.e. the conversion without isolation of the compound of formula V, takes place in a simpler manner and, besides dimethyl sulphoxide, there can also be used other polar solvents such as, for example, ethylene glycol, dimethylformamide, diglyme and the like. In fact, any conventional inert organic polar solvent can be utilized in carrying out this conversion.

As mentioned earlier, the furanone of formula I is a known substance and can be used, inter alia as a starting material for the manufacture of optically active R-(31 )-pantolactone. This conversion can be carried out, for example, in accordance with the following Reaction Scheme:

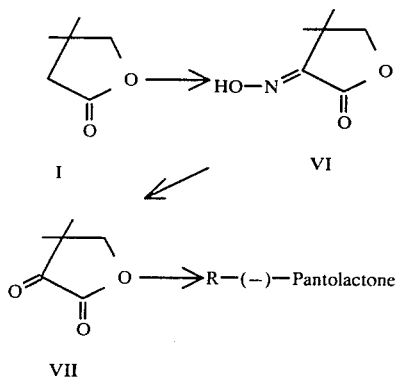

The oxime formation, i.e. the conversion of the furanone of formula I into the oxime of formula VI, can be carried out in a manner known per se, i.e. in an analogous manner to the formation of oximes from esters. This is conveniently carried out by reaction with a strong base such as an alkali metal hydride or alkaline earth metal hydride, e.g. lithium hydride, sodium hydride, potassium hydride, calcium hydride and the like. Further alkali metal amides such as, for example, sodium amide, potassium amide and the like can also be used. The amount of base conveniently amounts to from about 0.9 to about 2 and preferably about 1.4 equivalents. The oxime formation is also conveniently carried out in an inert organic solvent and at a temperature of about 0° C. to about 40° C., preferably of about 5° C. to about 10° C. As solvents there can be named here, for example: aliphatic or aromatic hydrocarbons such as, for example, hexane, benzene, toluene and the like or also ethers such as, for example, diethyl ether, dioxan and the like. Hexane is a preferred solvent. Furthermore, the oxime formation can also be carried out in the presence of the usual nitrites, preferably in the presence of lower alkyl nitrites with about 1 to 5 carbon atoms. The amount of nitrite conveniently amounts to from about 1 to about 2 and preferably about 1.1 to 1.2 equivalents.

The conversion of the oxime of formula VI into the ketopantolactone of formula VII can be carried out in a manner known per se. Surprisingly, however, it has been established that in the present case this conversion can also be carried out by simply adding a mineral acid such as, for example, hydrochloric acid or sulphuric acid and at a temperature of about 0° C. to about 40° C., preferably at about room temperature. Thus, it has been found that after adding the mineral acid to the oxime the ketopantolactone formed can be extracted readily with a suitable organic solvent. As especially suitable solvents there can be named, for example: halogenated hydrocarbons such as methylene chloride or carbon tetrachloride or also aromatic hydrocarbons such as, for example, benzene, toluene, xylene and the like. Methylene chloride and toluene are preferably used.

The oxime of formula VI can be isolated from the reaction mixture after its formation or can be processed further in situ.

The ketopantolactone of formula VII is a known compound and can be converted into R-(−)-pantolactone in a known manner, e.g. by asymmetric hydrogenation.

EXAMPLE 1

104.15 g of 2.2-dimethyl-1,3-propanediol (1 mol) are suspended in 200 ml of methylene chloride in a 500 ml four-necked flask which is provided with a stirrer, a reflux condenser, a thermometer and a dropping funnel. 125 g (1.05 mol) of thionyl chloride are added dropwise within 1 hour while stirring at 5°-10° C. The reaction mixture is then warmed to 40° C. for 3 hours. The thusobtained oil is washed with 50 ml of water and then with 50 ml of NaHCO₃ solution and dried over Na₂SO₄. After removing the majority of methylene chloride on a rotary evaporator the residue is distilled at 85°-87° C./30 mmHg over a 10 cm isolated column filled with Raschig rings. There are obtained 142.5 g of 5,5-dimethyl-1,3,2-dioxathiane 2-oxide in the form of a colourless oil.

EXAMPLE 2

30 g (0.198 mol) of 5,5-dimethyl-1,3,2-dioxathiane 2-oxide (prepared in accordance with Example 1) and 15.5 g (0.317 mol) of dry, finely powdered NaCN in 40 ml of dry dimethyl sulphoxide are added while gassing with argon to a 350 ml four-necked flask which is provided with a stirrer, a reflux condenser and a thermometer. The reaction mixture is stirred at 100° C. for 30-36 hours. The majority of the dimethyl sulphoxide (35-36 ml) is then distilled off cautiously at 65°-70° C./3 mmHg over a 5 cm Vigreux column. The residue is suspended in 130 ml of water and the suspension is brought to pH 3 with about 16 ml of 25% HCl solution. The black mixture is extracted continuously with 80 ml of isopropyl ether. After drying over Na₂SOt₄ and removing the solvent on a rotary evaporator the product is distilled over a 5 cm Vigreux column at 75°-82° C./0.2 mmHg. There are obtained 16 g of 4-hydroxy-3,3-dimethyl-butyronitrile in the form of an oil.

EXAMPLE 3

79.4 g (0.701 mol) of 4-hydroxy-3,3-dimethyl-butyronitrile (prepared in accordance with Example 2) and 400 ml of 25% HCl solution are placed in a 750 ml four-necked flask which is provided with a stirrer, a reflux condenser and a thermometer. The mixture is stirred at 75° C. for 5 hours and then extracted continuously with 200 ml of methylene chloride. After drying over Na₂SO₄ the solvent is concentrated on a rotary evaporator. The thus-obtained crude product is distilled over a Hickmann apparatus at 71°-76° C./8 mmHg. There are obtained 76 g of 4,5-dihydro-4,4-dimethyl-2(3H)-furanone as a glassy substance.

EXAMPLE 4

10 g (0.067 mol) of 5,5-dimethyl-1,3,2-dioxathiane 2-oxide (prepared in accordance with Example 1), 70 ml of methylene chloride, 0.76 g (0.0033 mol) of benzyltriethylammonium chloride and 70 ml of water are placed in a 350 ml four-necked flask which is provided with a stirrer and a thermometer. 7.5 g (0.0475 mol) of KMnO₄ are added portion-wise at 5°-10° C. and while stirring vigorously. After the addition the reaction mixture is stirred at room temperature for a further 30 minutes and suction filtered. The organic phase is separated. The residue is washed well on the suction filter with 20 ml of methylene chloride and the aqueous phase is again extracted with this new filtrate. The combined organic phases are extracted with 1 g of NaHSO₃ in 20 ml of water and washed with a small amount of water.

After drying over Na₂SO₄ and evaporation there are obtained 10.2 g of 5,5-dimethyl-1,3,2-dioxathiane 2,2-dioxide as a white powder with a m.p. of 80°–82° C.

EXAMPLE 5

45 g (0.271 mol) of 5,5-dimethyl-1,3,2-dioxathiane 2,2-dioxide and 23.9 g (0.49 mol) of dry, finely powdered NaCN in 200 ml of ethylene glycol are placed in a 750 ml four-necked flask which is provided with a stirrer, a condenser and a thermometer. This mixture is stirred at 75° C. for 15 hours. 400 ml of 36% HCl solution are then added at room temperature. The mixture is subsequently heated at 75° C. for 4 hours. The reaction mixture is cooled to room temperature and suction filtered. The filtrate is extracted four times with 150 ml of methylene chloride each time. The combined organic phases are washed twice with 50 ml of water each time, dried over Na₂SO₄ and evaporated. The thus-obtained crude product is distilled at 87°–92° C./18 mmHg over a 4 cm Vigreux column. There are obtained 26.1 g of 4,5-dihydro-4,4-dimethyl-2(3H)-furanone as a glassy substance.

EXAMPLE 6

15 g (131.4 mmol) of 4,5-dihydro-4,4-dimethyl-2(3H)-furanone (prepared in accordance with Example 3 or Example 5) and 5.88 g (184 mmol. 1.4 eg.) of sodium hydride 75% are suspended in 140 ml of hexane while gassing with argon in a 250 ml four-necked flask which is provided with a stirrer, a thermometer, a 100 ml dropping funnel and a dry ice condenser. 10.84 (145 mmol, 1.1 eq.) of ethyl nitrite dissolved in 70 ml of hexane are added dropwise thereto within 15 minutes at 10°–15° C. The reaction mixture is then left to warm slowly, whereby a regular evolution of about 3 liters of hydrogen results within 2–4 hours. When required, the temperature is held at 30° C. by means of ice. The reaction mixture is added dropwise rapidly to 150 ml of 5% HCl and stirred for 15 minutes. The hexane phase is separated and the aqueous phase is extracted four times with 100 ml of methylene chloride. The combined organic phases are dried over Na₂SO₄ and evaporated on a rotary evaporator. There are obtained 17.1 g of crude product which contains 14.2 g of (E)-dihydro-4,4-dimethyl-2-(3H)-furanone-3-oxime and 2.6 g of educt. This educt is removed by bulb-tube distillation at 70°–80° C./0.1 mmHg. The crystalline residue is suspended in about 60 ml of toluene, filtered off under suction and dried. There are obtained 13.1 g of pure product with a melting point of 170°–173° C.

EXAMPLE 7

25 g of (E)-dihydro-4,4-dimethyl-2(3H)-furanone-3-oxime (prepared in accordance with Example 6) in 250 ml of 37% HCl are added to a 500 ml round flask which is provided with a magnetic stirrer. The mixture is stirred for 2 hours and then extracted with methylene chloride using a Keberle extractor. After drying over Na₂SO₄ the solvent is removed on a rotary evaporator, whereby a crude product crystallizes. This crude product is distilled at 63°–66° C./0.1 mmHg in an apparatus which is provided with an air cooler and there are obtained 18.9 g of dihydro-4,4-dimethyl-2,3-furandione with a melting point of 64°–67° C.

I claim:

1. A process for the manufacture of the furanone of the formula

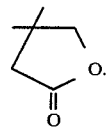

which process comprises reacting the diol of the formula

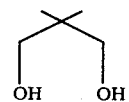

with thionyl chloride to give the compound of the formula

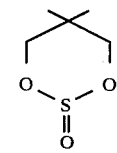

if desired, oxidizing this compound to give the compound of the formula

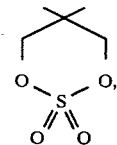

reacting the compound of formula III or IV with sodium cyanide and hydrolyzing the thus-obtained compound of the formula

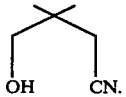

2. A process for producing a compound of the formula:

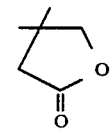

comprising reacting a compound of the formula

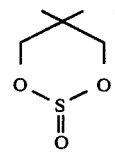

with sodium cyanide in an inert organic solvent medium to form a compound of formula:

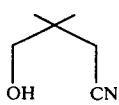   V and then hydrolyzing said compound of formula V to produce the compound of formula I.

3. The process of claim 2 wherein said reaction with sodium cyanide and said hydrolysis are carried out in the same organic solvent medium.

4. The process of claim 3 wherein said organic solvent medium contains dimethyl sulfoxide.

5. A process of producing a compound of the formula:

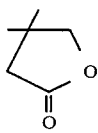   I comprising reacting a compound of the formula:

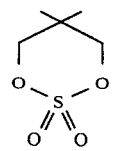   IV with sodium cyanide in an inert organic medium to form a compound of the formula

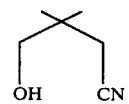   V and thereafter hydrolyzing said compound of formula V to produce the compound of formula I.

6. The process of claim 5 wherein said reaction with sodium cyanide and said hydrolysis is carried out in the same solvent medium.

7. The process of claim 6 wherein said reaction with sodium cyanide is carried out in dimethyl sulfoxide.

* * * * *